(12) United States Patent
Taylor et al.

(10) Patent No.: US 8,623,591 B2
(45) Date of Patent: *Jan. 7, 2014

(54) METHOD FOR SEPARATING DESIRED CELLS FROM TISSUE BY FREEZING

(75) Inventors: Michael J. Taylor, Mount Pleasant, SC (US); David E. Pegg, York (GB)

(73) Assignee: Lifeline Scientific, Inc., Itasca, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,536

(22) Filed: Aug. 27, 2012

(65) Prior Publication Data

US 2012/0322045 A1 Dec. 20, 2012

Related U.S. Application Data

(63) Continuation of application No. 12/654,147, filed on Dec. 11, 2009, now Pat. No. 8,252,589.

(60) Provisional application No. 61/121,957, filed on Dec. 12, 2008.

(51) Int. Cl.
*A01N 1/00* (2006.01)

(52) U.S. Cl.
USPC .......................................................... 435/1.3

(58) Field of Classification Search
None
See application file for complete search history.

(56) References Cited

U.S. PATENT DOCUMENTS 8,252,589 B2 * 8/2012 Taylor et al. ................... 435/378

FOREIGN PATENT DOCUMENTS

WO  WO 2008/031957 A2  3/2008

OTHER PUBLICATIONS

Taylor et al., "Interaction of Cooling Rate, Warming Rate, and Extent of Permation of Cryoprotectant in Determining Survival of Isolated Rat Islets of Langerhans During Cryopreservation", Diabetes 36 : 59-65 (1987).*
Taylor et al., "Selective Killing of Leucocytes by Freezing: Potential for Reducing the Immunogenicity of Pancreatic Islets," Diabetes Research, vol. 5, pp. 99-103, 1987.
Bank, "A High Yield Method for Isolating Rat Islets of Langerhans Using Differential Sensitivity to Freezing," Cryobiology, vol. 20, pp. 237-244, 1983.
Peters et al., "Enrichment of Mutants of *Mucor racemosus* by Differential Freeze-killing," Journal of General Microbiology, vol. 105, pp. 77-81, 1978.
Apr. 23, 2010 International Search Report and Written Opinion in corresponding International Patent Application No. PCT/US2009/067942.
Taylor et al., "Cryo-Isolation" A Novel Method for Enzyme-Free Isolation of Pancreatic Islets Involving in Situ Cryopreservation of Islets and Selective Destruction of Acinar Tissue, Transplantation Proceedings 43 : 318-3183 (2011).

* cited by examiner

*Primary Examiner* — Sandra Saucier
(74) *Attorney, Agent, or Firm* — Oliff & Berridge, PLC

(57) ABSTRACT

Methods of isolating cellular products, such as pancreatic islets, may be used in diabetes research and therapeutic transplantation. The methods may involve providing a tissue having desired cells that are less prone to destructive freezing and undesired cells that are more prone to destructive freezing, or pre-treating a tissue to have such characteristics. The methods may involve freezing the tissue, disrupting the tissue, warming the tissue, and separating the desired cells from undesired cellular material to obtain the cellular product. The methods may thereby provide an enzyme-free or reduced-enzyme method of isolating a cellular product that is more consistent, reliable and less toxic than conventional methods. The methods may also yield an optimum quantity of cellular product that retain sufficient functional integrity to be useful as a transplantation resource.

18 Claims, 3 Drawing Sheets

METHOD FOR SEPARATING DESIRED CELLS FROM TISSUE BY FREEZING

CROSS-REFERENCE TO RELATED APPLICATION

This is a Continuation of application Ser. No. 12/654,147, filed Dec. 11, 2009, which claims the benefit of U.S. Provisional Application No. 61/121,957, filed Dec. 12, 2008, the entire disclosures of which are incorporated herein by reference in their entireties.

BACKGROUND

In modern medicine, cellular therapies, regenerative medicine and tissue engineering all involve technologies for harvesting, expanding, modifying and re-implanting live viable cells and tissues. A primary example is the transplantation of isolated pancreatic islets of Langerhans for the treatment of Type I (insulin dependent) diabetes. The process of harvesting the donor cells requires the controlled separation of the desired therapeutic cells from other unwanted cells in the donor tissue.

Historically, islet isolation methods have relied upon crude cutting of the tissue into fragments, which fails to separate the target cells from the unwanted cells. Today, the field of islet transplantation relies upon enzymatic digestion processes that destroy the extracellular matrix of the tissue, releasing the entrapped islets for further processing and purification. This widely practiced procedure has drawbacks due principally to the difficulty of controlling the digestive process to yield an optimum quantity of viable cells. Moreover, the process is harsh and even toxic, causing some inevitable loss of valuable cells. Furthermore, the process relies upon the purest forms of the enzymes, which are very expensive and still subject to batch variations that have led to variability and inconsistency in attempts to optimize and standardize these processes.

SUMMARY

Methods are disclosed for isolating cellular products that avoid, or reduce, the need for enzymatic digestion of the cellular product and instead rely upon the susceptibilities of cells to freezing injury to effect the separation of desired tissue from undesired tissue by virtue of a facilitated differential freezing and cryopreservation technique.

In embodiments, a cellular product is isolated by methods comprising providing a tissue having desired cells that are less prone to destructive freezing and undesired cells that are more prone to destructive freezing, freezing the tissue, disrupting the tissue, warming the tissue, and separating the desired cells from undesired cellular material to obtain the cellular product.

In embodiments, the cellular product is isolated by methods comprising pre-treating a tissue such that desired cells are less prone to destructive freezing and undesired cells are more prone to destructive freezing, freezing the tissue, disrupting the tissue, warming the tissue, and separating the desired cells from undesired cellular material to obtain the cellular product.

In embodiments, islets of a pancreas are isolated by methods comprising infusing islet tissue with a cryoprotectant solution comprising a cryoprotective agent (CPA) via a vascular system, infusing the acinar tissue with an aqueous solution via a ductal system, freezing the pancreas, disrupting the pancreas, warming the pancreas, and separating the islets.

In embodiments, pancreatic islet tissue that retains sufficient functional integrity to be useful as a transplantation resource is isolated by methods comprising surgically preparing an ex vivo pancreas for vascular and ductal cannulation, cooling the pancreas to about 4° C. to about 7° C., equilibrating islet tissue with a cryoprotective agent, infusing the pancreas with an aqueous solution by ductal flush to promote extensive ice formation upon freezing, freezing the pancreas to a temperature from about −10° C. to about −200° C., mechanically disrupting the pancreas while keeping the pancreas frozen, thawing the pancreas by immersion in medium to dilute out the CPA, filtering the pancreas, washing the pancreas, and gradient purifying or culturing the islet tissue.

Additional features and advantages of the present invention are described in, and will be apparent from, the following detailed description of embodiments.

DETAILED DESCRIPTION OF EMBODIMENTS

Figure 1A:
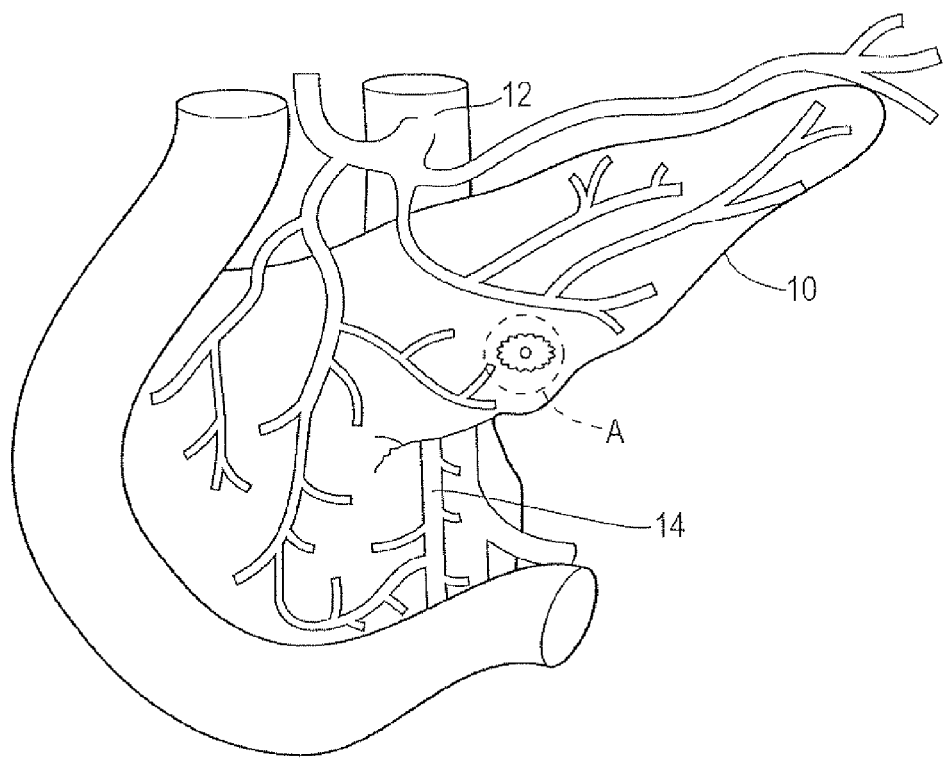
FIGS. 1A and 1B depict pancreas pre-treatment for cryo-isolation of islet tissue.

Embodiments of the invention provide an enzyme-free or reduced-enzyme method of isolating cellular products that is more consistent, reliable and less toxic than methods that primarily rely on enzyme digestion. Embodiments provide a method that can yield an optimum quantity of desired cells that retain sufficient functional integrity to be useful as a transplantation resource.

Embodiments of methods disclosed herein may be used to isolate any cellular product for therapeutic use and research, as long as the desirable and undesirable cells have, or can be pre-treated to promote, a differential freezing response. Such methods may allow frozen tissue to be banked and shipped in a frozen state and supplied to an end-user intact, lessening the susceptibility of desired cells to ischemic injury.

In embodiments, a cellular product may be isolated by providing a tissue having desired cells that are less prone to destructive freezing and undesired cells that are more prone to destructive freezing. The tissue may have inherent differential freezing properties to allow destruction of some cells and preservation of other cells during destructive freezing. For example, the tissue may comprise cells having different nucleation temperatures at which the cells become by freezing, such as desired cells having a lower freezing temperature than undesired cells.

In embodiments, the cellular product may be isolated by pre-treating a tissue such that desired cells are less prone to destructive freezing and undesired cells are more prone to destructive freezing. For example, the desired cells may become less prone to destructive freezing by infusing desired cells with a cryoprotective agent (CPA), and the undesired cells may become more prone to destructive freezing by infusing the undesired cells with solution that does not contain a CPA. The tissue may then be frozen and disrupted such that the desired cells are separated from undesired cellular material to obtain the cellular product. The tissue may be warmed and the desired cells separated from undesired cellular material to obtain a cellular product comprising the desired cells.

In embodiments, cryopreservation is used to selectively preserve the desired cells and destroy the undesired cells. Cryopreservation is a complex process of coupled heat and mass transfer, generally executed under non-equilibrium conditions. Simply freezing cells or tissues generally results in dead, nonfunctional materials.

During slow cooling, water is removed from cells and tissues as ice begins to form in the extracellular environment. The transformation of water into ice outside of the cell causes an osmotic imbalance that results in the exosmosis of water to the extracellular region where it is frozen into ice. Water loss continues until temperatures are reached at which the diffusion of water across the membrane becomes negligible. The amount of water loss from the cell is dependent upon the cooling rate after the formation of extracellular ice. Slow rates prolong the exosmosis of cellular water to the extracellular space and, therefore, produce greater cellular dehydration. Excessive dehydration leads to a series of cell injury mechanisms that are classified as "solution effects" that include exposure to increasingly toxic concentrations of electrolytes caused by removal of water from the liquid phase and membrane damage from excessive cell shrinkage.

During rapid freezing, the period of water exosmosis is shortened as membrane permeability to water quickly decreases with temperature. Water becomes trapped within the cell and the cytoplasm begins to supercool as the resulting thermodynamic imbalance of water increases.

Finally, the intracellular water equilibrates thermodynamically with the extracellular solution resulting in a phase change that transforms the intracellular water to ice. Widespread formation of intracellular ice in the cell has been uniformly associated with lethal cell injury.

For most cell types there exist optimal cooling rates that lead to maximum cell viability. These cooling rates provide sufficient cellular dehydration to prevent the formation of intracellular ice without causing excessive water loss that may lead to cell injury via "solution effects."

Warming cells from cryopreserved states is typically performed with maximal warming rates to prevent the recrystallization of ice from smaller ice crystals as the sample temperature is raised from cryogenic levels to the melting point of the solution. Recrystallization during rewarming is deleterious and results in lower cell viability although the exact mechanisms of injury are not fully understood. However, viability is generally greater when cells are warmed rapidly through the conditions in which recrystallization occurs.

The use of CPAs during freezing and thawing of biological materials is known. A wide variety of CPAs are used, with DMSO being the most widely used. Such chemicals are usually divided into two classes: (1) intracellular CPAs with low molecular weights, which permeate into cells, and (2) extracellular CPAs with relatively high molecular weights (greater than or equal to that of sucrose 342 daltons), which do not penetrate cells. The primary mode of protection for permeating CPAs is the displacement of intracellular water by the CPA. Regulated removal of intracellular water is essential to inhibiting lethal formation of intracellular ice.

Frozen tissues undergo extensive extracellular ice formation even during procedures that result in otherwise excellent cell viability. While routine histopathology methods usually do not permit detection of ice after thawing, cryosubstitution techniques can reveal the location of ice within the tissues. Using these techniques has demonstrated significant extracellular matrix distortion and damage. The extent of freezing damage depends upon the amount of free water in the system and the ability of that water to crystallize during freezing.

For purposes of illustration, the following description specifically describes embodiments related to isolating pancreatic islets. However, a person of ordinary skill in the art would understand that other embodiments are not limited to pancreatic cells.

Figure 1B:
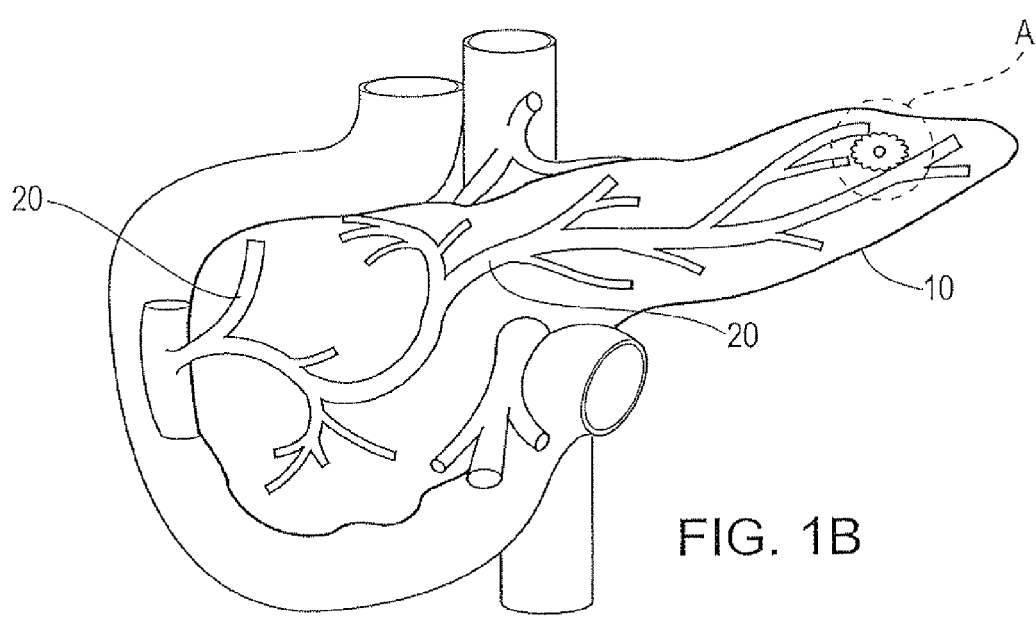
Figure 1C:
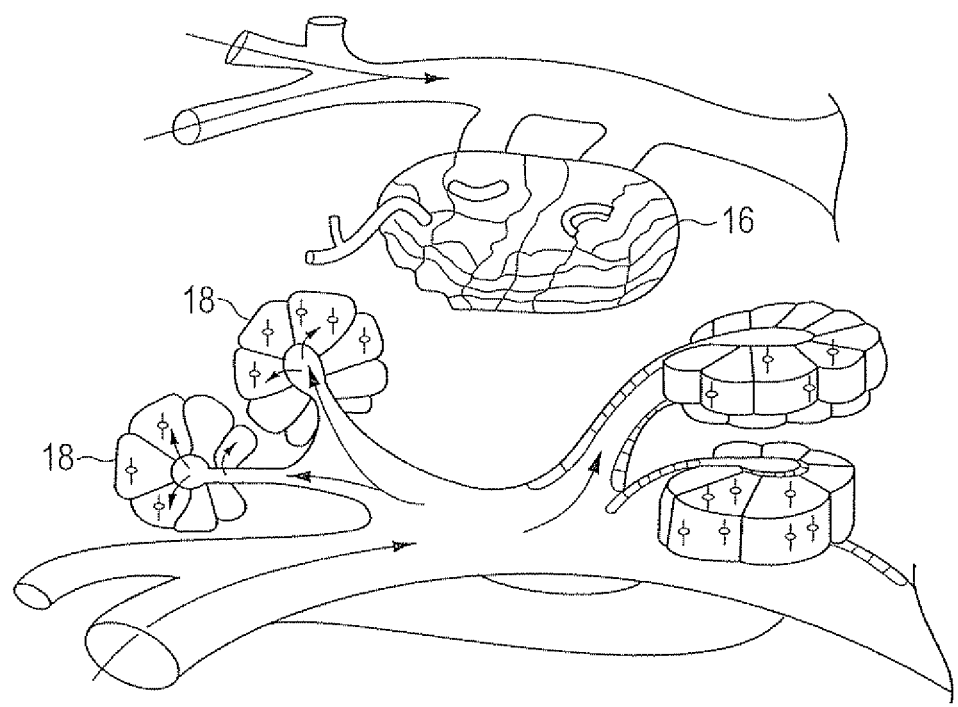
FIG. 1C depicts a blown-up view of the section defined by broken line A of FIGS. 1A and 1B.
Figure 2A:
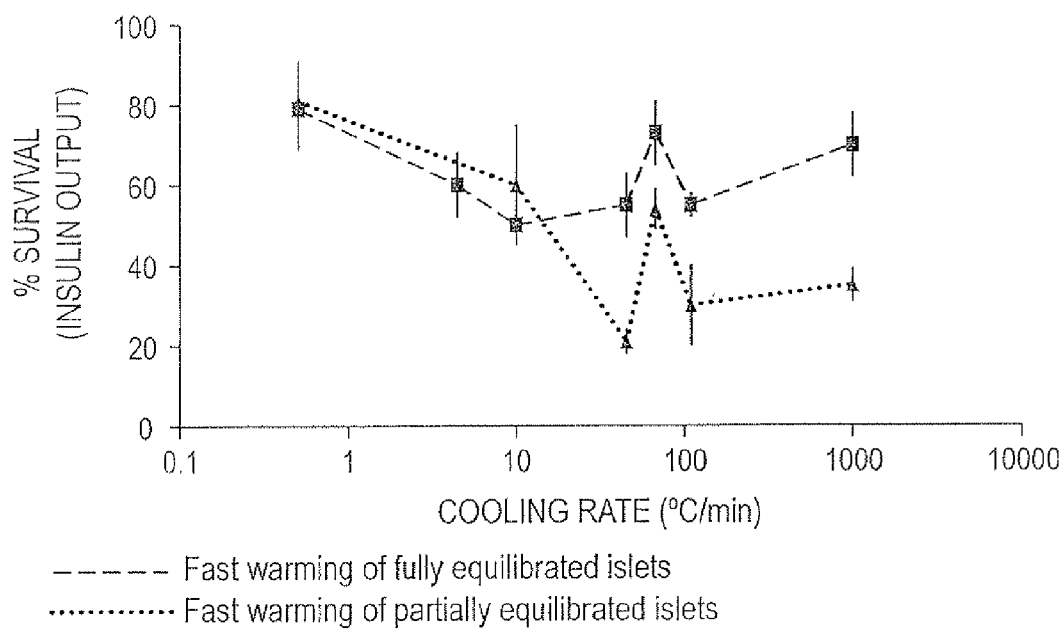
FIGS. 2A and 2B depict islet tissue survival as a function of dimethyl sulfoxide ("DMSO") permeation with varying freezing and warming rates.
Figure 2B:
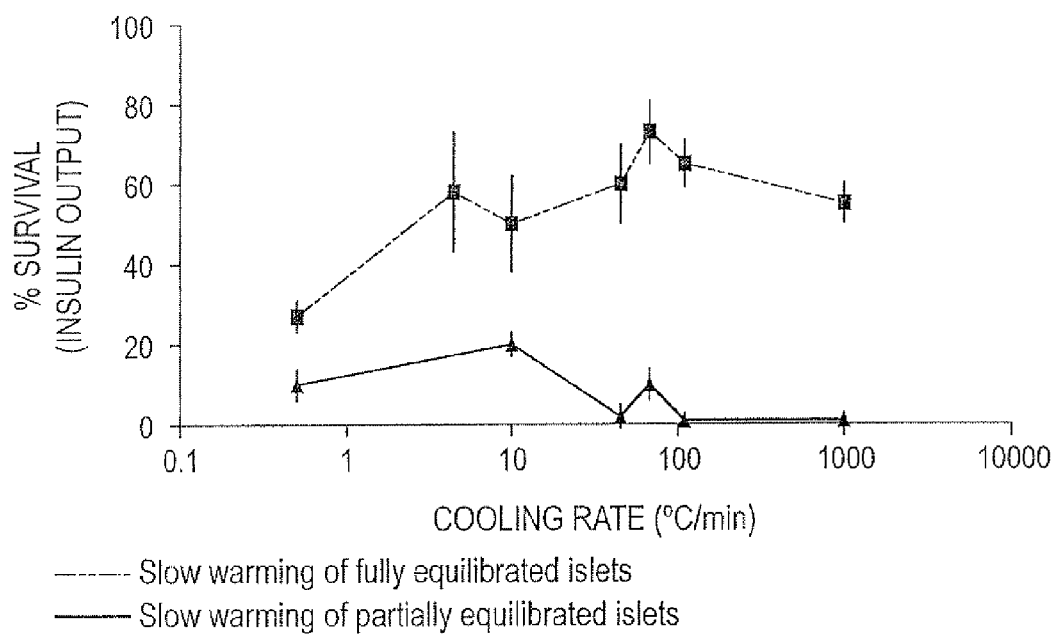

In embodiments, as depicted in FIGS. 1A, 1B and 1C, the method comprises pre-treating pancreas 10 such that islet tissue 16 is less prone to destructive freezing and acinar tissue 18 is more prone to destructive freezing. Pancreas 10 may be pre-treated by differential perfusion such that the destruction of acinar tissue 18 is maximized while islet tissue 16 is preserved. For example, islet tissue 16 may be infused with a cryoprotectant solution comprising a CPA via a vascular system, such as through celiac trunk 12 and superior mesenteric artery 14. After adequate equilibration of islet tissue 16, acinar tissue 18 may be infused with an aqueous solution through pancreatic ducts 20.

In embodiments, pre-treating the pancreas may occur under controlled conditions to preferentially equilibrate the islet tissue within the pancreas gland. For example, the vascular infusion may be performed at a temperature of from about 2° C. to about 35° C. Furthermore, perfusion should be maintained sufficiently long to allow equilibration of the islet tissue, but not the whole gland, with the permeating CPA. For example, perfusion may be maintained for a period of about 20 min. to about 70 min., such as about 25 to 35 min. or about 30 min. The rationale for this step is to deliver sufficient CPA to the islet tissue to protect it against freezing injury during subsequent freezing of the pancreas.

In embodiments, the cryoprotectant solution may comprise a CPA in an aqueous solution, such as a buffered biological medium. The CPA may, for example, be selected from the group consisting of DMSO, glycerol, ethylene glycol, propylene glycol, sucrose and trehalose. It has been found that DMSO is a better CPA than glycerol, and CPAs at concentrations from about 0.5 to about 3.0 molar are often particularly effective in minimizing cell damage in biological systems frozen with slow cooling rates.

In embodiments, the acinar tissue may be infused with an aqueous solution, such as water or isotonic saline. Retrograde infusion of the aqueous solution into the pancreatic duct may be initiated immediately upon completion of the vascular infusion of the islet tissue described above. The rationale for this step is to impregnate the acinar tissue with the aqueous solution to facilitate extensive destructive ice formation in the non-cryoprotected acinar tissue upon cooling and freezing.

The infusion of the acinar tissue may preferably be continued under controlled conditions until the pancreatic gland is impregnated with the aqueous solution to promote extensive ice formation upon freezing, for example, until the gland is visibly distended. For example, about 300 to about 400 ml of water or isotonic saline may be infused at a pressure of about 100 to about 120 mmHg for about 5 to about 10 min. in a pressure controlled system.

In embodiments, the method next comprises freezing the pancreas. The pancreas may be cooled to sub-zero temperatures until frozen. The rationale for this step is to maximize ice formation in the unprotected tissue to facilitate tissue disruption for subsequent disintegration of the pancreatic gland to release the cryoprotected islet tissue.

In embodiments, the pancreas may be frozen to a temperature of from about −10° C. to about −200° C., such as from about −40° C. to about −170° C., or from about −80° C. to about −130° C. In embodiments, freezing the pancreas may occur at a cooling rate of from about 1° C./min. to about 20°

C./min., such as from about 6° C./min. to about 15° C./min. In embodiments, the cooling rate may be from about 0.5° C./min. to about 5° C./min.

The rate of freezing the pancreas coupled with a rapid warming rate during warming of the pancreas may provide optimum conditions for recovery of functional islet tissue. In the example depicted in FIG. 1A, freezing at 11° C./min. correlates with more than 50% survival of islet function when the islets were warmed quickly after full or partial equilibration with 2 molar DMSO. FIG. 1A further indicates that survival may increase to about 80% if freezing is reduced to about 1° C./min. and warming is rapid. FIG. 1B illustrates that slow warming is detrimental (about 20% survival) for the exemplary slowly frozen islets irrespective of whether the islets are fully or partially equilibrated with the CPA. Warming of the pancreas may be achieved by, in embodiments, direct immersion in a warm medium, such as an osmotically-buffered medium.

It is also understood that the extent of equilibration with CPA may not be critical, especially when heat exchange is optimized towards fast warming coupled with slow freezing. This may be beneficial because the conditions for full equilibration of islets in situ may not be easily determined in relation to the requirement for minimal permeation of the CPA into the exocrine cells.

In embodiments, a liquid nitrogen supply system may be used for freezing the pancreas. In order to enhance fracturing of the pancreas, volumetric warming can be combined with liquid nitrogen freezing, with the addition of a compressed-air heat exchanger immersed in a hot water bath. This enables thawing of the gland without the need to remove it from the platform. Gland fracturing may occur during warming.

In embodiments, it may be advantageous to use supplemental low doses of a digestive enzyme to assist in final connective tissue dispersion if freezing and fracturing is not completely efficient in allowing release of cryoprotected islets from the disrupted tissue. In the case that a quick release of the frozen pancreas at cryogenic temperatures will be considered beneficial, the probes may be heated momentarily, to quickly thaw only a thin layer of the pancreas surrounding the probes and reduce the likelihood that the probes will adhere to the pancreas.

In embodiments, the pancreas is disrupted to release cryopreserved islet tissue from the disintegrated acinar tissue. Disrupting the pancreas may be performed while the pancreas is frozen or while the pancreas is warming. In embodiments, the disruption may be achieved by mechanical stress, thermo-mechanical stress induced by differential expansion, thermo-mechanical stress induced by steep temperature gradients, and thermo-mechanical stress induced by volume change upon freezing, or a combination thereof.

Thermo-mechanical stress is the outcome of the tendency of material to contract upon freezing, which may be driven by three different effects: volume change upon freezing as described above, steep temperature gradients, and differential expansion in composite materials. In practice, two or more of the above effects may be acting in concert. It is explained below how these effects may be harnessed to drive fracturing in embodiments.

The effect of steep temperature gradients: Most materials tend to contract with decreasing temperature (an exception is the anomalous behavior of water during phase transition). When a temperature gradient develops, adjacent layers of the material tend to contract at different rates. To make the actual contraction of adjacent layers compatible, mechanical strains will develop, which cause stresses in the material. When the temperature gradients lead to stresses that exceed the strength of the frozen material, fractures will form.

The effect of differential thermal expansion: Even when the temperature is uniform across the organ, but changes with time for the entire organ, fractures may develop due to the tendency of different material to contract at different rates.

In embodiments, the frozen pancreas has two major regions after pre-treatment: regions filled with an isotonic solution, and regions filled with CPA, where, given the morphology of the pancreas, many small CPA regions may be trapped within large frozen isotonic solution regions. In addition, material discontinuities, such as at islet surfaces, or between connective tissue and other gland constituents, can contribute to the structural damage due to differential thermal expansion and contraction. In the solid state—when the entire organ is at extreme low temperatures—material discontinuities may have little effect on fracture progression.

In moderate cryogenic temperatures, however, fractures may be less devastating to islets, which partially behave like a viscous material due to the presence of the CPA. The viscosity of a vitrified CPA increases exponentially with the decreasing temperature, but the viscosity value up to about 10° C. above the glass transition temperature should allow for the CPA to behave like a fluid or liquid in any practical time scale. A moderate cryogenic temperature range in this context is bounded by the freezing point of pure water (0° C.) as an upper limit, and the glass transition temperature of the CPA as a lower limit (around −123° C. for DMSO). For example, the thermal contraction of CPA can be three times as high as that of pure water, which is likely to affect the distribution of stress and, therefore, the pattern of fracturing around islets.

In other embodiments, disrupting the pancreas may be achieved by mechanically fracturing the frozen tissue. For example, this may be accomplished in two stages. The first stage may be to physically split the frozen pancreas into pieces, for example, with a hammer and chisel. The second stage may be to grind the frozen tissue pieces while immersed in warm water or isotonic medium, for example, by using an electric ice crusher or blender. This also serves to effect rapid warming and dilution of the cryoprotectant at the same time as mechanically grinding the tissue.

In embodiments, the method further comprises separating the islets from the undesired pancreatic material. Separation of the islet tissue may be achieved, for example, by filtration, density gradient separation, tissue culture, or a combination thereof. Filtration may be performed using a filtration apparatus, such as a stainless steel mesh (tea strainer). Separation may include washing the filtered pancreas with a medium containing a protease inhibitor, such as PEFABLOC®, and a deoxyribonuclease, such as PULMOZYME®, such that harmful endogenous proteases and DNA from lysed exocrine tissue are removed. In embodiments, the filtered pancreas may be stained with an indicator for identifying islets, such as dithizone, and examined under the microscope for the presence of intact islet tissue.

The separated islet tissue may not be cleanly cleaved from the acinar tissue and not all of the islet tissue may be completely intact. For example, some islet tissue may have a diffuse or loose structure that could reflect osmotic shock due to direct immersion into an aqueous medium during warming of the pancreas. In embodiments, such a problem may be averted by employing osmotic buffering during elution of the CPA from the islet tissue during or after thawing of the pancreas. Utilizing the osmotic buffering technique in embodiments may protect the structure of the islet tissue and minimize osmotic swelling and lysis during efflux of the permeating CPA. In contrast, osmotic buffering does not impact the simultaneous destruction and lysis of the acinar cells because these cells have not been protected by CPA permeation.

To further produce sufficiently clean cleavage of islet tissue, the cryoisolation method described above may, in embodiments, be combined with a mild enzyme digestion to purify the islet tissue. Another approach may be to use tissue culture as a modality for the "clean-up" process since the residual acinar tissue injured during the cryo-isolation process will die and disintegrate in culture.

Examples are set forth hereinbelow and are illustrative of different compositions and conditions that can be utilized in practicing embodiments. All proportions are by weight unless otherwise indicated. It will be apparent, however, that the disclosure can be practiced with many types of compositions and can have many different uses in accordance with the disclosure above and as pointed out hereinafter. For example, these Examples will be readily recognized by those having ordinary skill in the art as also being applicable to isolating human islets because pig pancreas is an art-recognized model for human pancreas.

Pig pancreas is a useful model for at least the following reasons: (1) pig pancreas provides a suitable model for critical heat and mass transfer parameters, (2) pig pancreas is a large animal model, (3) pigs are regarded as the most promising source of islets for future clinical xenografting, and (4) pig pancreas can be separated surgically into two independent perfusable lobes permitting comparative treatments using a single pancreas and avoiding the influence of animal/tissue variability.

EXAMPLE 1

Surgical Preparation of Pig Pancreas for Whole-Organ and Split-Lobe Perfusion

Following in situ cold flushing with organ preservation solution, the pancreas is removed from the donor with a duodenal segment attached around the pancreas head to protect the superior and inferior pancreaticoduodenal arteries. During perfusion preparations the pancreas is maintained cold, on ice. The common bile duct and pancreatic duct openings are part of the duodenum segment. The splenic vein and artery on the spleen side are ligated prior to spleen detachment. A 5-7 cm long aortic segment is left attached to the pancreas for future organ cannulation for whole pancreas perfusion. The segment includes the openings of both superior mesenteric artery (SMA) and celiac trunk (CT) vessels. All exposed arterial branches on the margin of gastroduodenal and hepatic sides of the pancreas are meticulously identified and ligated to ensure uniform perfusion throughout the gland and allow the effluent to emerge only from the portal vein. The pancreatic duct is cannulated using its opening on the duodenum side to preserve all early duct branches and to ensure subsequent good organ distension for gland digestion and islet isolation.

For whole pancreas perfusion a seal ring cannula (ORS, Des Plaines, Ill.) is placed on the aortic patch cut from the aortic segment inclusive of SMA and CT openings, without interfering with the two vessel lumens. This cannulation provides a sealed flow link between the pancreas and perfusion system. The aortic patch cannula is attached to the pump infusion port.

For lobular perfusion, the pancreas is carefully spit into the head and tail lobes. The pancreas is cut in two at the celiac trunk location and proximal to the SMA, with the latter being left with the tail lobe. For the latter, the splenic artery originating from the celiac trunk is straight cannulated for perfusion. If necessary, as the porcine donor anatomy will require, a second cannula can be placed on the superior mesenteric artery to facilitate tail lower part perfusion. For the head lobe ("c" shape) perfusion the gastroduodenal and/or hepatic artery is straight cannulated for perfusion. The duodenum remains attached to the organ during head lobe perfusion. The portal vein is equally split between the two lobes for appropriate effluent flow during perfusion. The cannulas used for straight cannulation of the two lobes are directly connected to the pump infusion port.

Conditions that may be selected for conducting the cryo-isolation of pig pancreatic islets are described below.

2 Molar DMSO is used as the CPA because it is widely used for islet cryopreservation. For the mode of vascular infusion of the CPA, the celiac/SMA is perfused using a seal-ring cannula and peristaltic pump for 30 min. at a temperature of 4° C. to 7° C. For the mode of ductal infusion of water, the pancreas is injected with water using a syringe via the pancreatic duct until the pancreas is visibly distended. During the freezing step, the pancreas is placed, with an embedded thermocouple, on a stainless steel tray supported above the surface of boiling liquid nitrogen at −196° C. The stainless steel tray provides a large surface area and thermal conductivity needed to cool a large infiltrated gland. For the mode of pulverization of the pancreatic tissue, the tissue is fractured via application of thermal shock by immersing frozen tissue directly into a warm medium. Alternatively, the tissue is mechanically sectioned in an electric ice grinder with a warm medium, which can facilitate fast warming and dilution.

Cryo-isolation of pancreatic islets conducted under the conditions described above results in a freezing rate of 11° C./min. and a final temperature in the frozen pancreas of less than −160° C. The solid frozen gland is divided into two sections to subject it to two different modes of disruption and warming. In the first, the frozen piece containing the thermocouple is immersed directly into warm (30° C.) tissue culture medium. This yields a warming rate of 12° C./min. but macroscopic fracturing is not achieved. It was therefore concluded that this mode of warming is less likely to produce the extensive thermal fracturing desired to shatter the tissue into small islet-containing fragments.

The second mode of disruption and warming comprises mechanically fracturing the frozen tissue in two stages. First, the frozen pancreas is physically split into pieces with a hammer and chisel. Second, the frozen tissue pieces are physically ground while immersed in warm medium.

The results obtained demonstrate the concept that differential freezing conditions can be applied to a single pancreas to effect in situ cryopreservation of intact islets while facilitating the destruction of surrounding acinar tissue.

EXAMPLE 2

Differential freezing techniques are used to selectively protect islets in situ during freeze destruction of the pancreas to disintegrate the gland and release viable islets. Specifically, ex vivo pancreas is first surgically prepared for vascular and ductal cannulation. In order to avoid the effects of animal to animal variation and to limit the number of pigs needed for a study, a split-lobe preparation is employed in which the pig pancreas is surgically prepared in such a way as to permit two independent perfusions of the tail and head as described below. Six replicants can be studied in both the control (conventional enzyme method) and the experimental (cryo-isolation) groups.

The pancreas is then cooled to a temperature of 4° C. to 7° C. and perfused with a CPA/Unisol mixture for 30 min. at a pressure of 10 mmHg. An individual islet represents the osmotic unit for equilibration, thus rapid equilibration (about less than 60 min.) can be expected. The pancreas parenchyma is infused with 300-400 ml of distilled water or saline by ductal flush at a pressure of 100-120 min Hg for 5-10 min, in a pressure control system. The pancreas is immediately frozen to −40° C. or less than −140° C. at a freezing rate of 1-10° C./min. to effect freezing of the pancreas while protecting the islets. The frozen tissue is mechanically disrupted to pieces for loading into a tissue blender (the tissue is kept frozen in this stage). Simultaneously, the tissue is thawed and chopped in a sucrose medium in the tissue blender. The product is then filtered through a stainless steel mesh, such as a tea strainer. This step removes large pieces of undisrupted exocrine tissue and stringy waste. The product is then wash blended with a medium containing PEFABLOC® and PULMOZYME®, thereby removing harmful endogenous proteases and DNA from lysed exocrine tissue. The product is gradient purified and/or cultured to purify the islets from the exocrine lysate.

The efficiency of cryo-isolation is evaluated in terms of the size distribution of islets and pancreatic fragments generated by the differential freezing process. This includes an assessment with dithizone staining of the fragments generated either with embedded islets or with fully cleaved, free islets and partially cleaved, so-called mantled islets. Relative efficiency of this baseline cryo-isolation technique is judged in comparison with conventional collagenase (e.g. LIBERASE, available from Roche, or collagenase available from Serva or VitaCyte) technique using controls within this disclosure as well as data from historical controls from pig pancreas isolations conventionally performed.

In embodiments, techniques for assessing isolated and purified islet tissue may include islet quantification, islet viability, and functional viability assessment using the glucose stimulated insulin secretion assay.

Islet Quantification: Following the procedures for islet isolation and purification, the total number of islets is determined using a counting graticule in the eyepiece of a dissecting microscope, and normalized to islet equivalents (IE). Islets are stained with dithizone, counted and converted to islet equivalents (IE). Counts performed in duplicate will be compared to counts performed using a computerized cell counter (e.g. IMAGEPRO® software). The purity of the islet preparation is assessed by comparison of dithizone-stained tissue to unstained exocrine tissue.

Islet Viability: Two principal assays are used to evaluate islet viability; a live/dead stain based upon the acridine orange/propidium iodide (AO/PI), or Syto Green/ethidium bromide fluorescent membrane integrity test and a metabolic assay based upon alamarBlue™. The AO/PI assay provides a semi-quantitative measure of islet integrity. In contrast, the alamarBlue™ assay is a quantitative method of non-invasively measuring islet viability in vitro and, because the reagent is non-toxic, the test can be performed on islets that are then subjected to further tests.

In vitro Assessment of Islet Function and Structure: Morphological assessment of tissue integrity and necrosis includes routine (H&E) staining, electron microscopy and apoptosis (TUNEL assay) in addition to parameters of oxidative stress (glutathione levels) and energetics (ATP assay). Insulin content and stimulated secretion assays may be carried out using conventional techniques.

EXAMPLE 3

This Example is directed to embodiments that supplement the cryo-isolation technique with an enzymatic digestion process by using a reduced concentration of collagenase. This is because completely enzyme-free cryo-isolation of islets may not provide a clean cleavage of islet tissue from the pancreas and a combination of mild enzyme digestion and cryo-isolation might yield a better product in some embodiments. Thus, methods incorporating a low dose of collagenase (e.g. LIBERASE, available from Roche, or collagenase available from Serva or VitaCyte) into the ductal perfusate prior to freezing the gland are desired. Replicate experiments are carried out using one half (0.7 mg/ml) and one tenth (0.14 mg/ml) the normal concentration of 1.4 mg/ml to determine the effect upon islet cleavage upon rewarming. This is assessed by comparing islet yield and the ratio of free, mantled and embedded islets as previously described. A total of 9 pigs permits inter-group comparisons with N=6 in each group listed in Table 1 below.

TABLE 1

| Porcine Donor ID | Group L0 Liberase conc = 0 | Group L1 Liberase conc = 0.7 mg/ml | Group L2 Liberase conc = 0.14 mg/ml |
| --- | --- | --- | --- |
| #1 | Head lobe | Tail lobe | — |
| #2 | — | Head lobe | Tail lobe |
| #3 | Tail lobe | — | Head lobe |
| #4 | Head lobe | Tail lobe | — |
| #5 | — | Head lobe | Tail lobe |
| #6 | Tail lobe | — | Head lobe |
| #7 | — | Head lobe | Tail lobe |
| #8 | Head lobe | Tail lobe | — |
| #9 | Tail lobe | — | Head lobe |
|  | N = 6 | N = 6 | N = 6 |

The experimental design described in Table 1 allows an equal distribution of head and tail portions of the pancreases to be assigned to each group. Assessment of the islet yield and cleavage parameters is determined immediately after rewarming and again after 24 hour culture at 37° C.

Collagenase Digestion Technique

The pancreas is distended with a solution containing a digestive enzyme, such as LIBERASE®. LIBERASE® (1.4 mg/ml) in serum-free solution is infused via the pancreatic duct. At this point, any extraneous tissue is dissected free of the pancreas. Next, the impregnated pancreas is cut into pieces and placed in a 450 ml stainless steel chamber, such as a Ricordi chamber that includes seven hollow stainless steel balls (Biorep Technologies, Inc., Miami) and a 500 micron pore-sized steel mesh positioned inside. The whole system is filled with Hanks Balanced Salts Solution (HBSS) via a tubing system that passes over a heat exchanger. The digestion temperature is then raised to 35±2° C. The solution is then recirculated at 200 ml/min and the digestion chamber is oscillated vertically at 300 oscillations/min with an amplitude of 1.8 cm. Frequent samples are stained with dithizone and examined under a microscope to gauge the extent of the digestion process. When adequate digestion has occurred, the digestion chamber is flushed with fresh cold HBSS and the islet solution collected in centrifuge tubes. The tubes are centrifuged at 55 g for two minutes at 4° C. in the presence of either fetal calf serum or excess calcium and magnesium to stop the enzymatic digestion process. The supernatant is drawn off and the tissue pellets, consisting of both exocrine and endocrine tissues, are washed in cold HBSS and then collected for separation. Purification of the islets is performed by density-gradient centrifugation using Ficoll/EuroCollins and a centrifuge, such as COBE® 2991. The latter allows for a continuous density gradient separation as specified by Roche. In this case, the Cabe hydraulic test is performed initially. Then the tubing is positioned in place, through the valves, from diaphragm to the rear of a steel weighted lid, to all lines. The desired Ficoll gradients are prepared in Euro-Collins. The pancreas digest pellet is resuspended in the first gradient (1.108) solution and pumped into the centrifuge (200 mL/min, for 3 minutes). After the solution loading completion, the air is purged from the centrifuge. Following, the centrifuge speed and the pump speed is set (1000 rpm and 50 ml/min, respectively), and the spinning process is started. When the desired speeds are reached, two other gradient solutions (1.096 and 1.037) are successively pumped in. After that a volume of 50 mL of HBSS is pumped, until the fluid reaches the rotary seal, and the excess pressure is released. The centrifuge is spun at room temperature, for 5 minutes. The centrifuge fractions are removed, and the islets are inspected for purity (using dithizone). The fractions are washed twice (spin for 2 minutes at 1200 rpm), the supernatant is removed and the cells are resuspended in culture media. The islets yield is then quantified.

What is claimed is:

1. A method, comprising:
    providing a tissue having desired cells that are less prone to destructive freezing and undesired cells that are more prone to destructive freezing, infusing the desired cells with a cryoprotectant solution comprising a cryoprotective agent, and infusing the undesired cells with solution that does not contain the cryoprotective agent;
    freezing the tissue;
    disrupting the tissue;
    warming the tissue; and
    separating the desired cells from undesired cellular material to obtain a product.

2. The method of claim 1, wherein the tissue is pancreatic tissue and the product is pancreatic islets.

3. The method of claim 2, further comprising treating the pancreatic islets with a digestive enzyme.

4. The method of claim 2, wherein freezing the pancreatic tissue comprises freezing the pancreas to a temperature of from about −10° C. to about −200° C.

5. The method of claim 2, wherein freezing the pancreatic tissue occurs at a cooling rate of from about 1° C./min. to about 20° C./min.

6. The method of claim 2, wherein warming the pancreatic tissue occurs at a warming rate of more than about 12° C./min.

7. The method of claim 2, wherein warming the pancreatic tissue is achieved by direct immersion of the tissue in a warm osmotically-buffered medium.

8. The method of claim 2, wherein disrupting the pancreatic tissue is achieved by a technique selected from the group consisting of mechanical stress, thermo-mechanical stress induced by differential expansion, thermo-mechanical stress induced by steep temperature gradients, and thermo-mechanical stress induced by volume change upon freezing, and combinations thereof.

9. The method of claim 2, wherein disrupting the pancreatic tissue is achieved while the pancreatic tissue is frozen or while the pancreatic tissue is thawing.

10. The method of claim 2, further comprising adding a collagenase to the pancreatic tissue at a concentration of less than 1.4 mg/ml.

11. The method of claim 2, wherein
    the pancreatic islets are infused with the cryoprotectant solution via a vascular system, and
    acinar tissue is infused with with the solution that does not contain the cryoprotective agent via a ductal system.

12. The method of claim 11, wherein the cryoprotective agent is selected from the group consisting of dimethyl sulfoxide, glycerol, ethylene glycol, propylene glycol, sucrose and trehalose.

13. The method of claim 11, wherein the aqueous solution is water or isotonic saline.

14. The method of claim 11, wherein infusing the pancreatic islets with the cryoprotectant solution is performed at a temperature of from about 2° C. to about 35° C. and for a period of about 20 to about 70 minutes.

15. The method of claim 11, wherein infusing the acinar tissue with an aqueous solution is continued until the pancreatic tissue is visibly distended.

16. The method of claim 11, wherein the cryoprotective agent is present in the cryoprotectant solution at a concentration of from about 0.5 molar to about 3.0 molar.

17. The method of claim 11, further comprising eluting the cryoprotective agent from the pancreatic islets and applying osmotic buffering to the pancreatic tissue during the elution of the cryoprotective agent from the pancreatic islets.

18. The method of claim 1, wherein infusing the desired cells with a cryoprotectant solution comprises pre-treating the tissue with the cryoprotectant solution until the desired cells equilibrate thermodynamically with the cryoprotective agent.

* * * * *